United States Patent
Matečić Mušanić et al.

(10) Patent No.: US 12,391,656 B2
(45) Date of Patent: Aug. 19, 2025

(54) SOLID STATE FORMS OF TAFAMIDIS AND SALTS THEREOF

(71) Applicant: ASSIA CHEMICAL INDUSTRIES LTD., Tel Aviv (IL)

(72) Inventors: Sanja Matečić Mušanić, Zagreb (HR); Valentina Travančić, Zagreb (HR); Dubravka Pavličić, Zagreb (HR)

(73) Assignee: ASSIA CHEMICAL INDUSTRIES LTD., Tel Aviv (IL)

( * ) Notice: Subject to any disclaimer, the term of this patent is extended or adjusted under 35 U.S.C. 154(b) by 888 days.

(21) Appl. No.: 17/610,195

(22) PCT Filed: May 15, 2020

(86) PCT No.: PCT/US2020/033039
§ 371 (c)(1),
(2) Date: Nov. 10, 2021

(87) PCT Pub. No.: WO2020/232325
PCT Pub. Date: Nov. 19, 2020

(65) Prior Publication Data
US 2022/0259162 A1      Aug. 18, 2022

Related U.S. Application Data

(60) Provisional application No. 62/927,913, filed on Oct. 30, 2019, provisional application No. 62/909,903, filed on Oct. 3, 2019, provisional application No. 62/871,249, filed on Jul. 8, 2019, provisional application No. 62/848,800, filed on May 16, 2019.

(51) Int. Cl.
C07D 263/57      (2006.01)
A61P 25/02      (2006.01)

(52) U.S. Cl.
CPC ............ *C07D 263/57* (2013.01); *A61P 25/02* (2018.01); *C07B 2200/13* (2013.01)

(58) Field of Classification Search
CPC ... C07D 263/57; A61P 25/02; C07B 2200/13; A61K 31/423
See application file for complete search history.

(56) References Cited

U.S. PATENT DOCUMENTS

| | | |
|---|---|---|
| 2017/0273953 A1 | 9/2017 | Girard et al. |
| 2018/0273499 A1 | 9/2018 | Shachantov et al. |

FOREIGN PATENT DOCUMENTS

| | | |
|---|---|---|
| CN | 102432559 A | 5/2012 |
| CN | 106715405 A | 5/2017 |
| CN | 109153656 A | 1/2019 |
| WO | 2016038500 A1 | 3/2016 |
| WO | 2019175263 A1 | 9/2019 |
| WO | 2021232619 A1 | 11/2021 |

OTHER PUBLICATIONS

Office Action issued by the CNIPA in corresponding Chinese Application No. 202080044108.4 dated Jun. 1, 2023 (7 pages) (English language translation not availabe).
Office Action issued by the Eurasian Patent Office in corresponding Application 202193136/28 dated Feb. 1, 2023 together with English language translation (6 pages).
Mino R. Caira, "Crystalline Polymorphism of Organic Compounds", Topics in Current Chemistry, vol. 198, pp. 163-208 (1998).
Byrn et al., "Pharmaceutical Solids: A Strategic Approach to Regulatory Considerations", Pharmaceutical Research, vol. 12, No. 7, pp. 945-954 (1995).
International Search Report and Written Opinion of the International Searching Authority issued in corresponding application PCT/US2020/033039 mailed Jul. 23, 2020 (17 pages).
Office Action issued in corresponding Korean application No. 10-2021-7041164 dated Mar. 10, 2025, together with English language translation.

*Primary Examiner* — Amy L Clark
*Assistant Examiner* — Chihyi Lee
(74) *Attorney, Agent, or Firm* — Carter, DeLuca & Farrell LLP

(57) ABSTRACT

The present disclosure relates to solid state forms of Tafamidis and salts thereof, processes for preparation thereof and pharmaceutical compositions thereof.

15 Claims, 9 Drawing Sheets

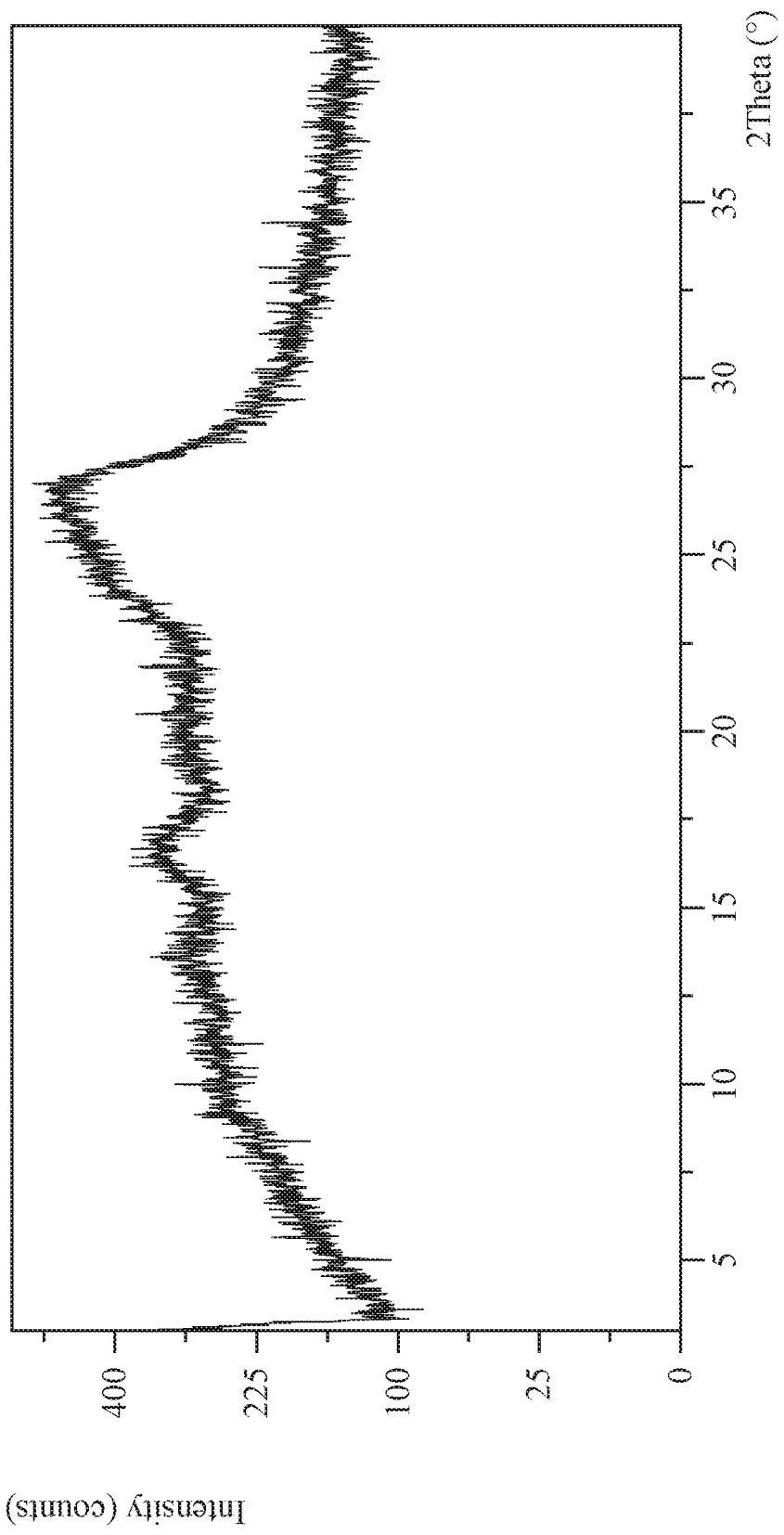
Figure 1 shows a PXRD pattern of tafamidis amorphous form

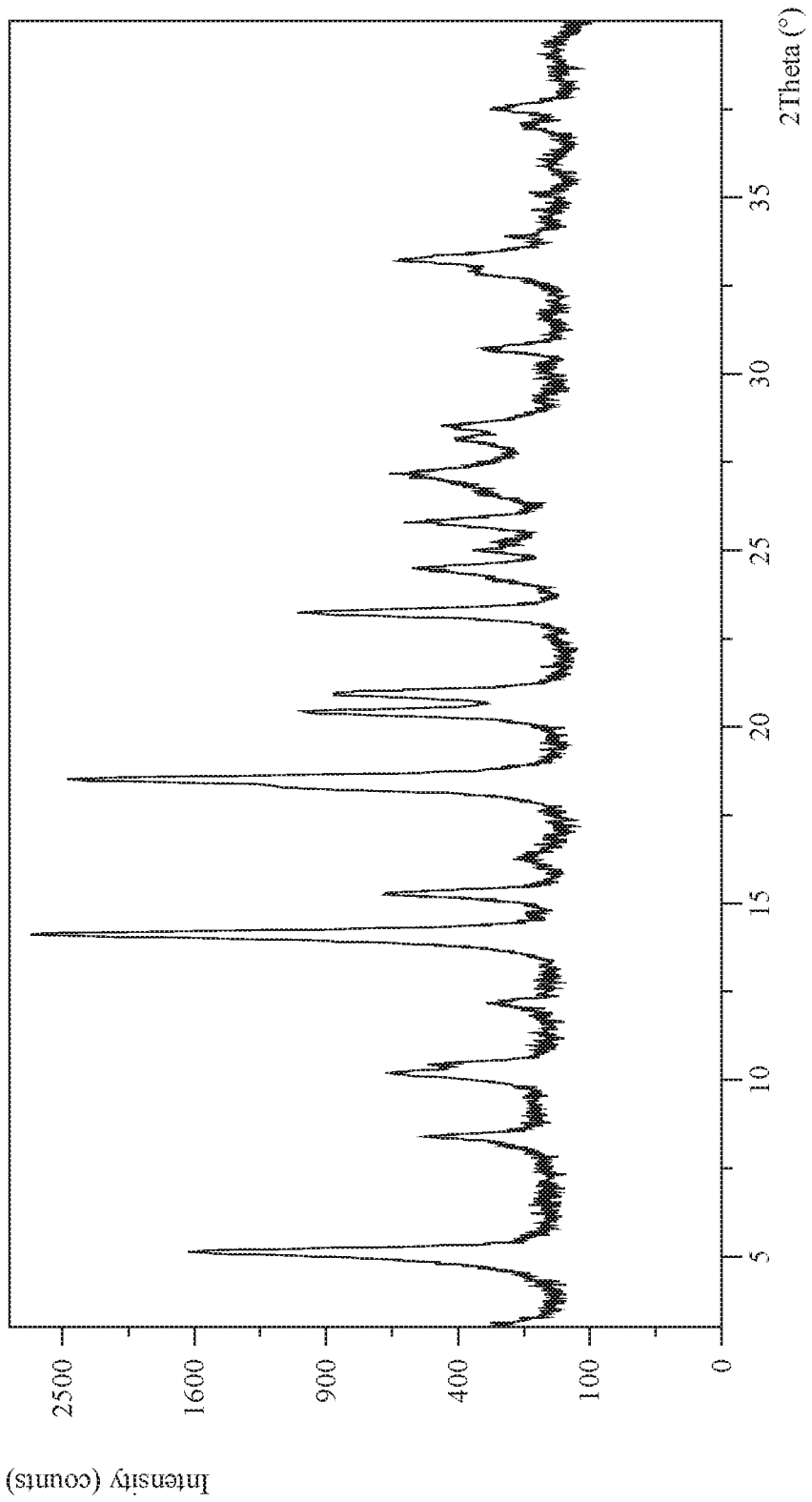
Figure 2 shows a PXRD pattern of tafamidis, Form I

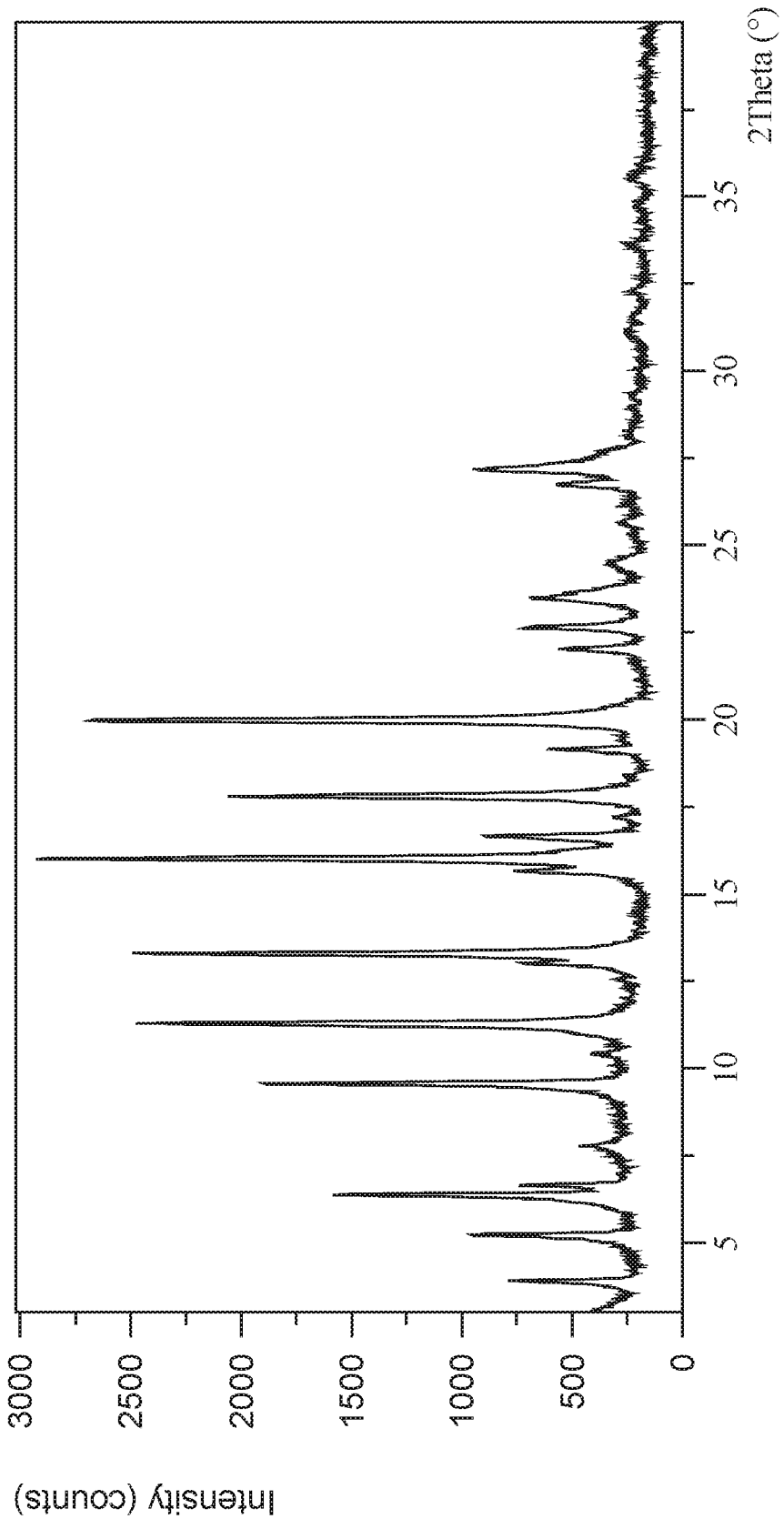

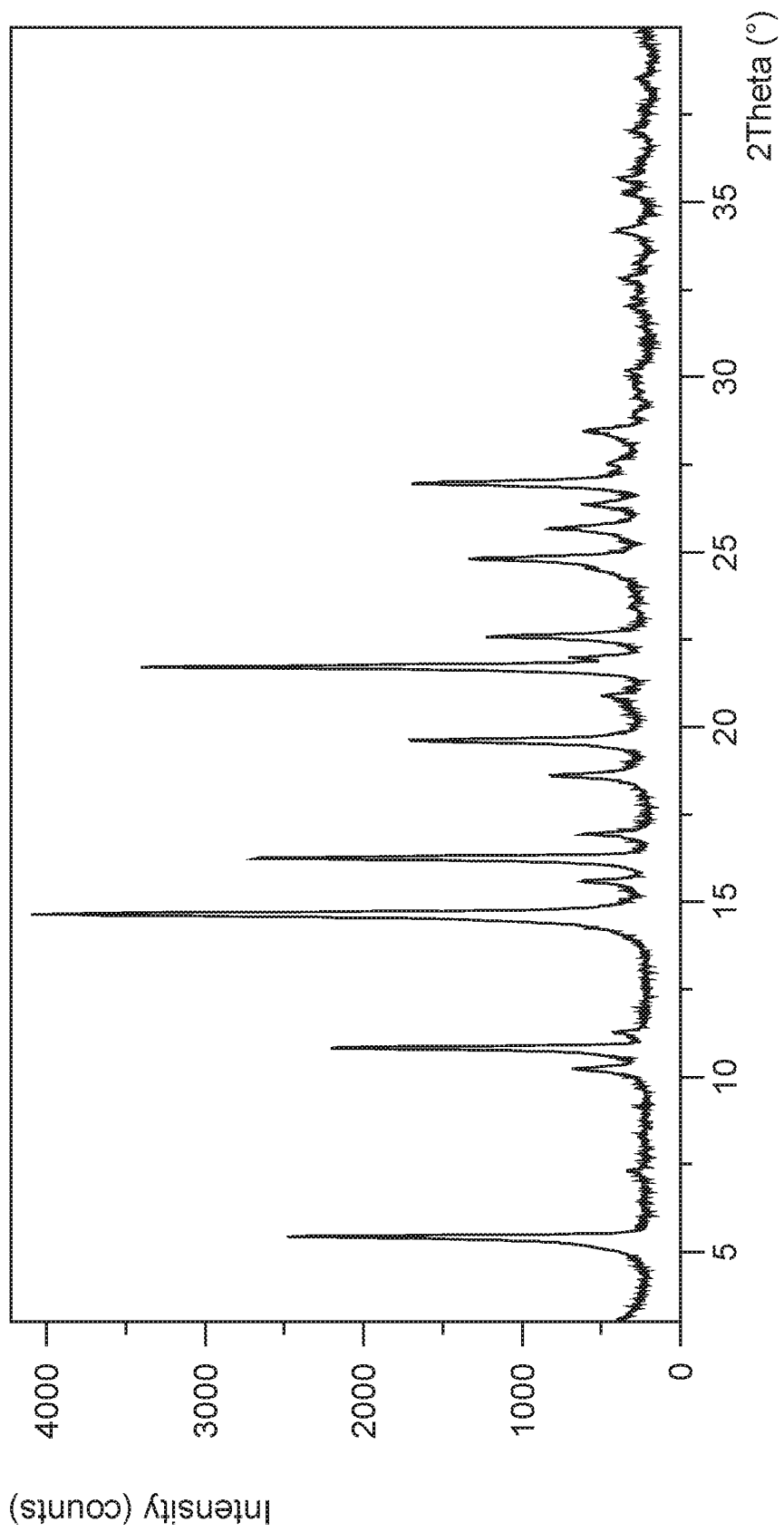
Figure 4 shows a PXRD pattern of tafamidis, Form III

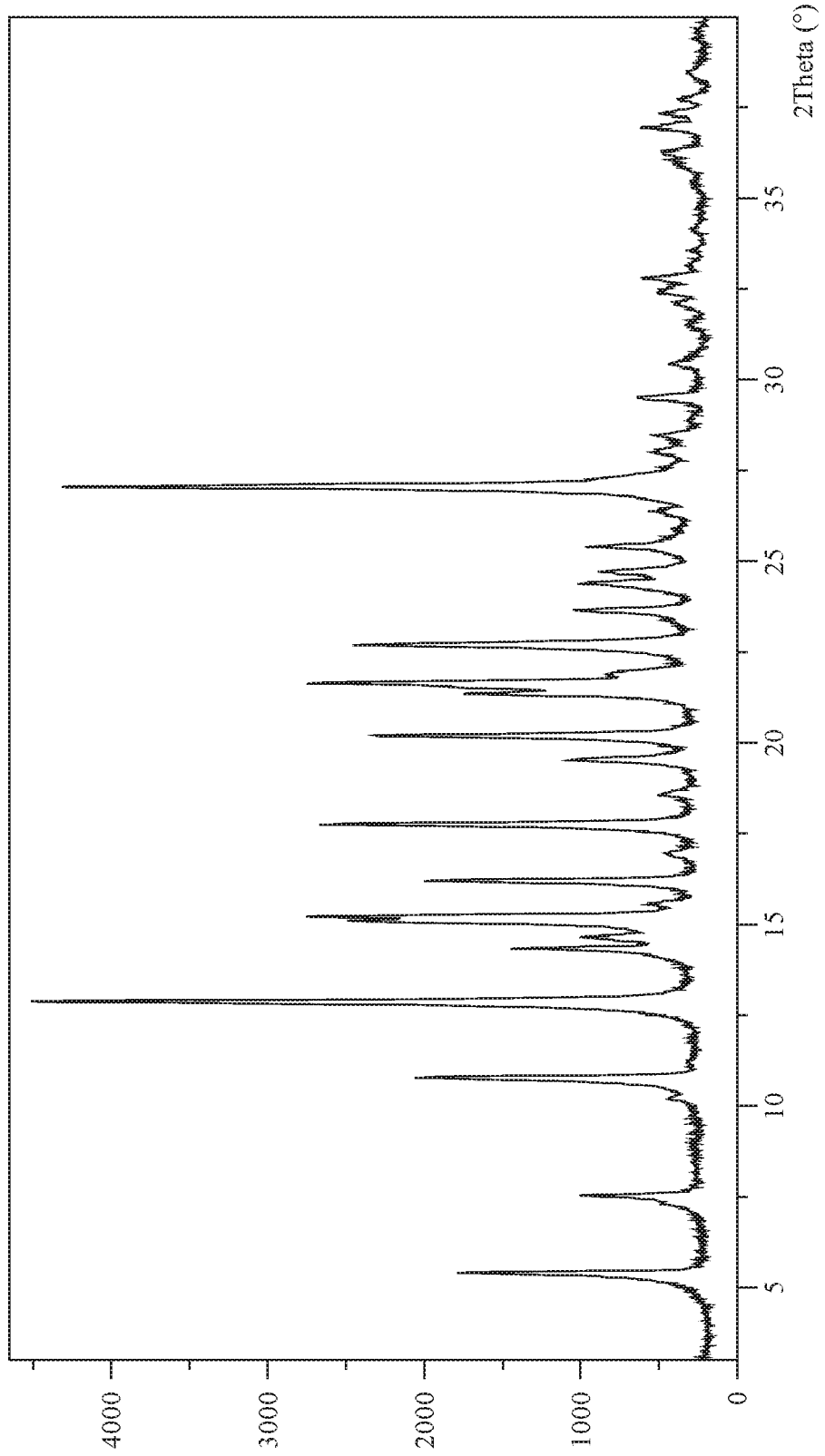

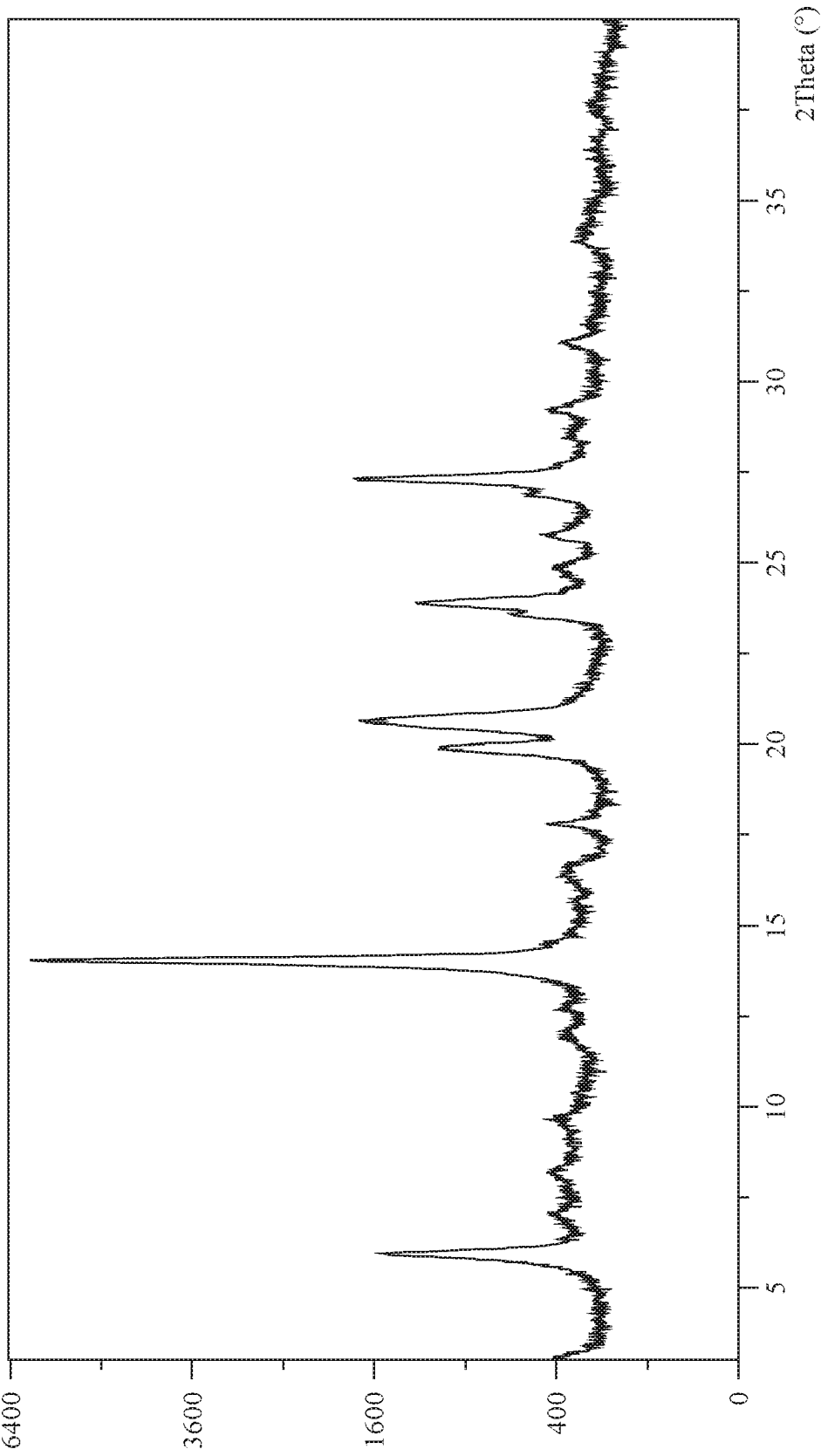
Figure 6 shows a PXRD pattern of tafamidis, Form V

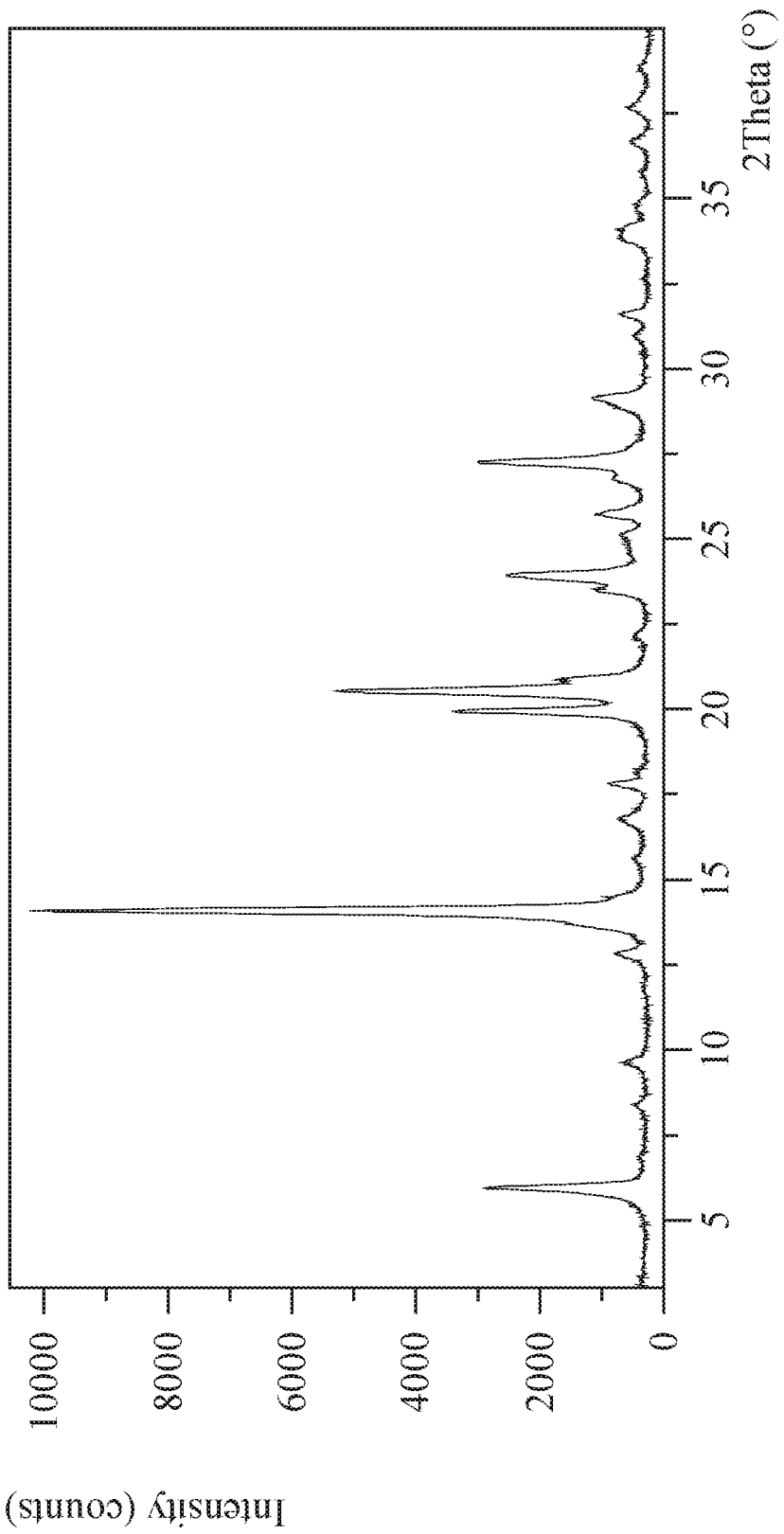
Figure 6A shows a PXRD pattern of tafamidis, Form V

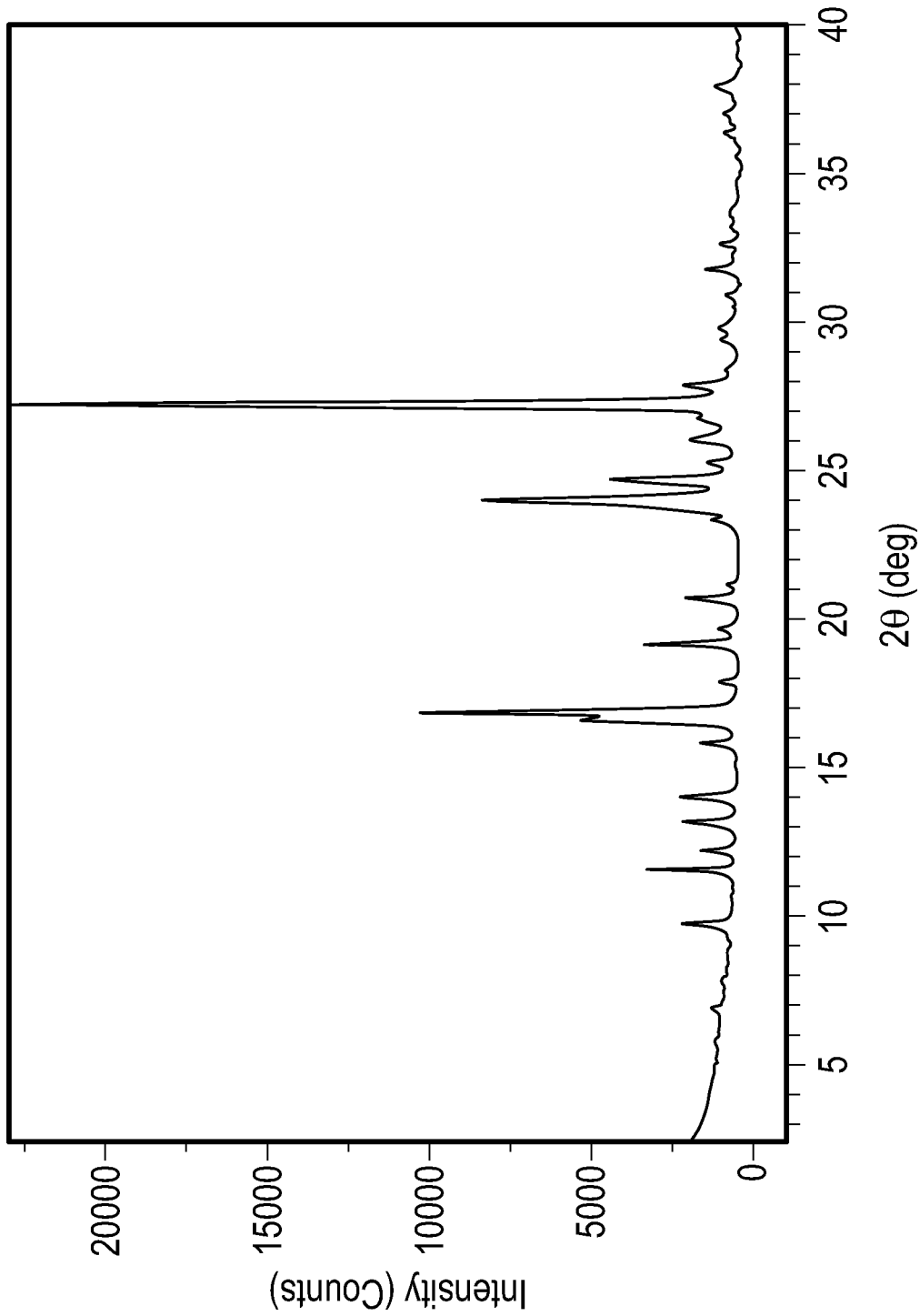

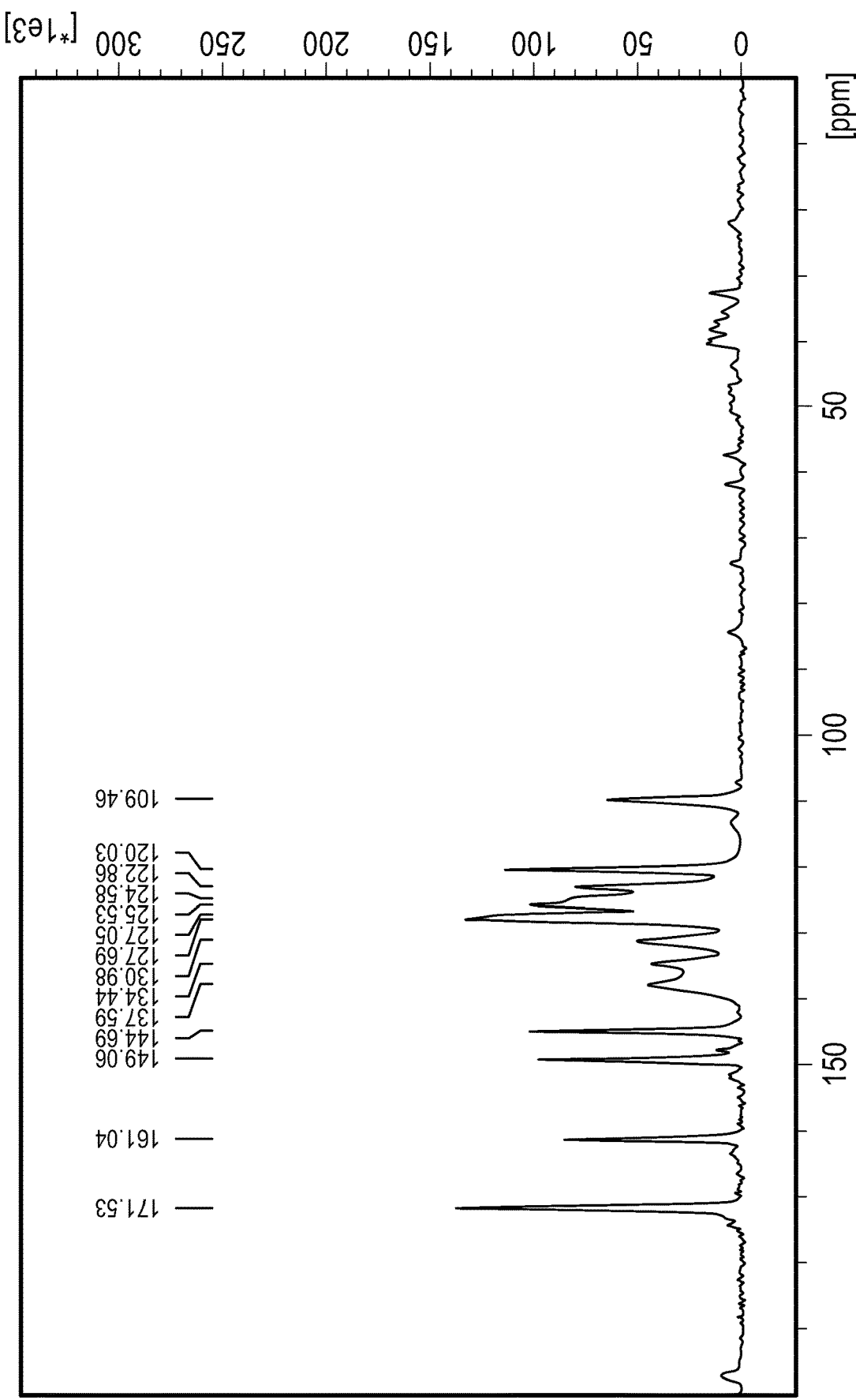

SOLID STATE FORMS OF TAFAMIDIS AND SALTS THEREOF

CROSS REFERENCE TO RELATED APPLICATIONS

This application is a National Stage of, and claims priority to and the benefit of, International Patent Application No. PCT/US2020/033039 filed May 15, 2020, which, in turn, claims the benefit of and priority to, U.S. Provisional Patent Application No. 62/848,800 filed May 16, 2019, U.S. Provisional Patent Application No. 62/871,249 filed Jul. 8, 2019, U.S. Provisional Patent Application No. 62/909,903 filed Oct. 3, 2019, and U.S. Provisional Patent Application No. 62/927,913 filed Oct. 30, 2019, the entire disclosures of each of which are incorporated by reference herein.

TECHNICAL FIELD

The present disclosure relates to solid state forms of Tafamidis and salts thereof, processes for preparation thereof and pharmaceutical compositions thereof.

BACKGROUND

Tafamidis has the chemical name 2-(3,5-dichlorophenyl)-1,3-benzoxazole-6-carboxylic acid. Tafamidis has the following chemical structure:

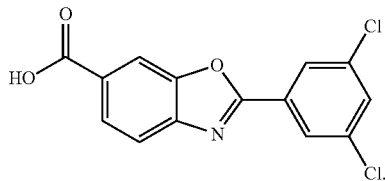 [SMILES: O=C(O)c1ccc2nc(-c3cc(Cl)cc(Cl)c3)oc2c1]

Tafamidis meglumine has the chemical name 2-(3,5-dichlorophenyl)-1,3-benzoxazole-6-carboxylic acid mono (1-deoxy-1-methylamino-D-glucitol). Tafamidis meglumine has the following chemical structure:

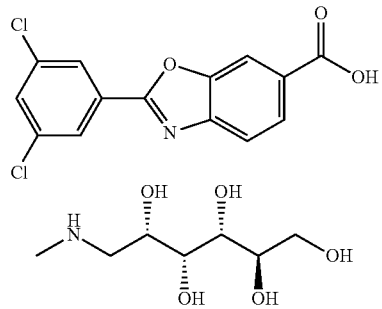

VYNDAQEL (tafamidis meglumine) and VYNDAMAX (tafamidis), are both capsules for oral administration and contain tafamidis as the active moiety. The U.S. Food and Drug Administration ("FDA") has approved VYNDAQEL and VYNDAMAX for the treatment of cardiomyopathy of wild type or hereditary transthyretin-mediated amyloidosis in adults to reduce cardiovascular mortality and cardiovascular-related hospitalization. EMA has approved VYNDAQEL for the treatment of transthyretin amyloidosis in adult patients with stage 1 symptomatic polyneuropathy to delay peripheral neurologic impairment.

Tafamidis is known from U.S. Pat. No. 7,214,695.

Solid state forms of tafamidis meglumine are known from U.S. Pat. No. 9,249,112, International Publication No. WO2017190682 and International Publication No. WO2019175263. Solid state forms of tafamidis are known from U.S. Pat. No. 9,770,441 and International Publication No. WO2019175263.

Polymorphism, the occurrence of different crystal forms, is a property of some molecules and molecular complexes. A single compound, like tafamidis, may give rise to a variety of polymorphs having distinct crystal structures and physical properties like melting point, thermal behaviors (e.g. measured by thermogravimetric analysis—"TGA", or differential scanning calorimetry—"DSC"), powder X-ray diffraction (PXRD) pattern, infrared absorption fingerprint, Raman absorption fingerprint, and solid state ($^{13}$C-) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, improving the dissolution profile, or improving stability (polymorph as well as chemical stability) and shelf-life. These variations in the properties of different salts and solid state forms may also provide improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new salts, solid state forms, and solvates of a pharmaceutical product can provide materials having desirable processing properties, such as ease of handling, ease of processing, storage stability, and ease of purification, or as desirable intermediate crystal forms that facilitate conversion to other salts or polymorphic forms. New salts, polymorphic forms and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity, or polymorphic stability, or solubility, which may offer better processing or handling characteristics, improved dissolution profile, or improved shelf-life.

For at least these reasons, crystalline forms (including solvated forms) of tafamidis and salts thereof having desirable properties remain desirable.

SUMMARY

The present disclosure relates to solid state forms of tafamidis and salts thereof, to processes for preparation thereof, and to pharmaceutical compositions including these solid state forms.

The present disclosure also provides uses of the solid state forms of tafamidis and salts thereof for preparing other solid state forms of tafamidis, tafamidis salts and solid state forms thereof.

In another embodiment, the present disclosure encompasses the above described solid state forms of tafamidis and salts thereof for use as a medicament, in embodiments for the treatment of transthyretin-mediated amyloidosis.

In another embodiment, the present disclosure encompasses methods for treating transthyretin-mediated amyloidosis with the use of the above described solid state form of tafamidis and salts thereof.

In a further embodiment, the present disclosure further provides the use of any of the solid state forms of tafamidis and salts thereof described according to any embodiment herein, for the preparation of a pharmaceutical composition or a pharmaceutical formulation of tafamidis, wherein the tafamidis in the pharmaceutical composition or formulation is in a solid form, wherein the solid form may be any crystalline form or an amorphous form.

The present disclosure further provides pharmaceutical compositions including the solid state forms of tafamidis and salts thereof according to the present disclosure.

In yet another embodiment, the present disclosure encompasses pharmaceutical formulations including the above described solid state forms of tafamidis and salts thereof and at least one pharmaceutically acceptable excipient, in embodiments for oral administration in dosage forms such as tablets, capsules, etc.

The present disclosure encompasses processes to prepare said pharmaceutical formulations of tafamidis by combining at least one of the above solid state forms and at least one pharmaceutically acceptable excipient.

The solid state forms as defined herein, as well as the pharmaceutical compositions or formulations of the solid state forms of tafamidis and salts thereof, can be used as medicaments, in embodiments for the treatment of transthyretin-mediated amyloidosis.

The present disclosure also provides methods of treating transthyretin-mediated amyloidosis, by administering a therapeutically effective amount of the solid state form of tafamidis and/or salts thereof of the present disclosure, or at least one of the above pharmaceutical compositions or formulations, to a subject suffering from transthyretin-mediated amyloidosis, or otherwise in need of the treatment.

The present disclosure also provides use of the solid state forms of tafamidis and salts thereof of the present disclosure, or at least one of the above pharmaceutical compositions or formulations, for the manufacture of a medicament for treating transthyretin-mediated amyloidosis.

BRIEF DESCRIPTION OF THE FIGURES

FIG. 1 shows a powder X-ray diffraction pattern ("powder XRD" or "PXRD") of tafamidis amorphous form.
FIG. 2 shows a PXRD of tafamidis form I.
FIG. 3 shows a PXRD of tafamidis form II.
FIG. 4 shows a PXRD of tafamidis form III.
FIG. 5 shows a PXRD of tafamidis form IV.
FIG. 6 shows a PXRD of tafamidis form V.
FIG. 6A shows a PXRD of tafamidis form V.
FIG. 7 shows a PXRD of tafamidis form 4.
FIG. 8 shows $^{13}C$ NMR of anhydrous form V of tafamidis.

DETAILED DESCRIPTION

The present disclosure relates to solid state forms of tafamidis and salts thereof, in embodiments to crystalline forms of tafamidis free acid, processes for preparation thereof, and pharmaceutical compositions including said solid state forms.

The solid state forms of tafamidis according to the present disclosure may have advantageous properties selected from at least one of: chemical or polymorphic purity, flowability, solubility, dissolution rate, bioavailability, morphology or crystal habit, stability-such as chemical stability as well as thermal and mechanical stability with respect to polymorphic conversion, stability towards dehydration and/or storage stability, a lower degree of hygroscopicity, low content of residual solvents, and advantageous processing and handling characteristics such as compressibility, or bulk density.

A crystal form may be referred to herein as being characterized by graphical data "as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of tafamidis and salts thereof referred to herein as being characterized by graphical data "as depicted in" a Figure will thus be understood to include any crystal forms of the tafamidis and salts thereof, characterized with the graphical data having such small variations, as are well known to the skilled person, in comparison with the Figure.

A solid state form (or polymorph) may be referred to herein as polymorphically pure or substantially free of any other solid state (or polymorphic) forms. As used herein in this context, the expression "substantially free of any other forms" will be understood to mean that the solid state form contains about 20% or less, about 10% or less, about 5% or less, about 2% or less, about 1% or less, or about 0% of any other forms of the subject compound as measured, for example, by PXRD. Thus, solid state forms of tafamidis and tafamidis salts, described herein as substantially free of any other solid state forms, would be understood to contain greater than about 80% (w/w), greater than about 90% (w/w), greater than about 95% (w/w), greater than about 98% (w/w), greater than about 99% (w/w), or about 100% (w/w) of the subject solid state form of tafamidis and/or tafamidis salts. Accordingly, in some embodiments of the disclosure, the described solid state forms of tafamidis and/or tafamidis salts may contain from about 1% to about 20% (w/w), from about 5% to about 20% (w/w), or from about 5% to about 10% (w/w) of one or more other solid state forms of the same tafamidis and/or tafamidis salts.

As used herein, unless stated otherwise, PXRD peaks reported herein are measured using $CuK_\alpha$ radiation, $\lambda=1.5418$ Å.

As used herein, the term "isolated" in reference to solid state forms of tafamidis and tafamidis salts of the present disclosure corresponds to solid state forms of tafamidis and tafamidis salts that are physically separated from the reaction mixture in which it is formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C. A process or step may be referred to herein as being carried out "overnight." This refers to a time interval, e.g., for the process or step, that spans the time during the night, when that process or step may not be actively observed. This time interval is from about 8 to about 20 hours, or about 10 to about 18 hours, in embodiments about 16 hours.

The term "solvate", as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

The crystal hydrate indicated by water analysis by Karl Fischer (KF) titration or by TGA analysis of the product is believed to have been produced as a result of water introduced from the atmosphere in which this material was processed, or by traces of water present in the solvents that were in contact with the material, or a combination of these factors.

The amount of solvent employed in a chemical process, e.g., a reaction or a crystallization, may be referred to herein as a number of "volumes" or "vol" or "V." For example, a material may be referred to as being suspended (or dissolved) in 10 volumes (or 10 vol or 10 V) of a solvent. In this context, this expression would be understood to mean milliliters of the solvent per gram of the material being suspended (or dissolved), such that suspending (or dissolving) 5 grams of a material in 10 volumes of a solvent means that the solvent is used in an amount of 10 milliliters of the solvent per gram of the material that is being suspended (or dissolved) or, in this example, 50 mL of the solvent. In another context, the term "v/v" may be used to indicate the number of volumes of a solvent that are added to a liquid mixture based on the volume of that mixture. For example, adding methyl tert-butyl ether (MTBE) (1.5 v/v) to a 100 ml reaction mixture would indicate that 150 mL of MTBE was added.

As used herein, the term "reduced pressure" refers to a pressure of about 10 mbar to about 50 mbar.

As used herein tafamidis form 4 is described in U.S. Pat. No. 9,770,441. U.S. Pat. No. 9,770,441 describes form 4 having a powder X-ray diffraction pattern comprising peaks at diffraction angles (2-theta) of 15.9±0.2, 16.9±0.2, 18.0±0.2, and 27.3±0.2. Alternatively said crystalline form has a powder X-ray diffraction pattern comprising peaks at diffraction angles (2-theta) essentially the same as shown in FIG. 7.

As used herein, unless stated otherwise, $^{13}C$ CP/MAS NMR spectra reported herein are measured at 125 MHz, preferably at a temperature of at 293 K±3° C.

The present disclosure encompasses an amorphous form of tafamidis. Tafamidis amorphous form can be characterized by a PXRD pattern as depicted in FIG. 1.

The present disclosure includes a crystalline form of tafamidis designated as form I. The crystalline form I of tafamidis can be characterized by data selected from one or more of the following: a PXRD pattern having peaks at 5.1, 8.4, 18.5, 21.0 and 25.8 degrees 2-theta±0.2 degrees 2-theta; a PXRD pattern as depicted in FIG. 2, and combinations of these data.

Crystalline form I of tafamidis may be further characterized by a PXRD pattern having peaks at 5.1, 8.4, 18.5, 21.0 and 25.8 degrees 2-theta±0.2 degrees 2-theta, and also having one, two, three, four or five additional peaks at 10.2, 10.5, 15.3, 24.4 and 27.1 degrees 2-theta±0.2 degrees 2-theta.

Crystalline form I of tafamidis may be characterized by each of the above characteristics alone or by all possible combinations, e.g., by a PXRD pattern having peaks at 5.1, 8.4, 18.5, 21.0 and 25.8 degrees 2-theta±0.2 degrees 2-theta and a PXRD pattern as depicted in FIG. 2.

Crystalline form I of tafamidis may alternatively be characterized by a PXRD pattern having peaks at 5.1, 8.4, 10.2, 10.5, 15.3, 18.5, 21.0, 24.4, 25.8 and 27.1 degrees 2-theta±0.2 degrees 2-theta.

Crystalline form I of tafamidis according to any of the above embodiments may be a hydrate.

The present disclosure includes a crystalline form of tafamidis designated as form II. The crystalline form II of tafamidis can be characterized by data selected from one or more of the following: a PXRD pattern having peaks at 3.9, 11.3, 13.3, 16.0 and 27.2 degrees 2-theta±0.2 degrees 2-theta; a PXRD pattern as depicted in FIG. 3 and combinations of these data.

Crystalline form II of tafamidis may be further characterized by a PXRD pattern having peaks at 3.9, 11.3, 13.3, 16.0 and 27.2 degrees 2-theta±0.2 degrees 2-theta, and also having one, two, three, four or five additional peaks at 5.3, 6.4, 17.8, 19.2 and 22.0 degrees 2-theta±0.2 degrees 2-theta.

Crystalline form II of tafamidis may be characterized by each of the above characteristics alone or by all possible combinations, e.g., by a PXRD pattern having peaks at 3.9, 11.3, 13.3, 16.0 and 27.2 degrees 2-theta±0.2 degrees 2-theta and a PXRD pattern as depicted in FIG. 3.

Crystalline form II of tafamidis may alternatively be characterized by a PXRD pattern having peaks at 3.9, 5.3, 6.4, 11.3, 13.3, 16.0, 17.8, 19.2, 22.0 and 27.2 degrees 2-theta±0.2 degrees 2-theta.

The present disclosure includes a crystalline form of tafamidis designated as form III. The crystalline form III of tafamidis can be characterized by data selected from one or more of the following: a PXRD pattern having peaks at 5.5, 10.9, 14.7, 19.6 and 21.7 degrees 2-theta±0.2 degrees 2-theta; a PXRD pattern as depicted in FIG. 4; and combinations of these data.

Crystalline form III of tafamidis may be further characterized by a PXRD pattern having peaks at 5.5, 10.9, 14.7, 19.6 and 21.7 degrees 2-theta±0.2 degrees 2-theta, and also having one, two, three, four or five additional peaks at 10.3, 11.3, 16.3, 18.6 and 25.7 degrees 2-theta±0.2 degrees 2-theta.

Crystalline form III of tafamidis may be characterized by each of the above characteristics alone or by all possible combinations, e.g., by a PXRD pattern having peaks at 5.5, 10.9, 14.7, 19.6 and 21.7 degrees 2-theta±0.2 degrees 2-theta and a PXRD pattern as depicted in FIG. 4.

Crystalline form III of tafamidis may alternatively be characterized by a PXRD pattern having peaks at 5.5, 10.3, 10.9, 11.3, 14.7, 16.3, 18.6, 19.6, 21.7 and 25.7 degrees 2-theta±0.2 degrees 2-theta.

Crystalline form III of tafamidis according to any of the above embodiments may be an acetic acid solvate.

The present disclosure includes a crystalline form of tafamidis designated as form IV. The crystalline form IV of tafamidis can be characterized by data selected from one or more of the following: a PXRD pattern having peaks at 7.5, 12.9, 15.1, 17.7 and 25.4 degrees 2-theta±0.2 degrees 2-theta; a PXRD pattern as depicted in FIG. 5; and combinations of these data.

Crystalline form IV of tafamidis may be further characterized by a PXRD pattern having peaks at 7.5, 12.9, 15.1, 17.7 and 25.4 degrees 2-theta±0.2 degrees 2-theta, and also having one, two, three, four or five additional peaks at 20.2, 21.3, 22.7, 23.7 and 27.0 degrees 2-theta±0.2 degrees 2-theta.

Crystalline form IV of tafamidis may be characterized by each of the above characteristics alone or by all possible combinations, e.g., by a PXRD pattern having peaks at 7.5, 12.9, 15.1, 17.7 and 25.4 degrees 2-theta±0.2 degrees 2-theta and a PXRD pattern as depicted in FIG. 5.

Crystalline form IV of tafamidis may alternatively be characterized by a PXRD pattern having peaks at 7.5, 12.9, 15.1, 17.7, 20.2, 21.3, 22.7, 23.7, 25.4 and 27.0 degrees 2-theta±0.2 degrees 2-theta.

Crystalline form IV of tafamidis according to any of the above embodiments may be an acetic acid solvate.

The present disclosure includes a crystalline form of tafamidis designated as form V. The crystalline form V of tafamidis can be characterized by data selected from one or more of the following: a PXRD pattern having peaks at 6.0, 19.9, 20.6, 23.9 and 29.2 degrees 2-theta±0.2 degrees 2-theta; a PXRD pattern as depicted in FIG. 6; and combinations of these data.

Alternatively, the crystalline form V of tafamidis can be characterized by data selected from one or more of the following: a PXRD pattern having peaks at 6.0, 19.9, 20.6, 23.9 and 29.2 degrees 2-theta±0.2 degrees 2-theta; a PXRD pattern as depicted in FIG. 6A; and combinations of these data.

Crystalline form V of tafamidis may be further characterized by a PXRD pattern having peaks at 6.0, 19.9, 20.6, 23.9 and 29.2 degrees 2-theta±0.2 degrees 2-theta, and also having one, two, three or four additional peaks at 17.8, 25.8, 27.3 and 31.1 degrees 2-theta±0.2 degrees 2-theta.

Crystalline form V of tafamidis may be characterized by each of the above characteristics alone or by all possible combinations, e.g., by a PXRD pattern having peaks at 6.0, 19.9, 20.6, 23.9 and 29.2 degrees 2-theta±0.2 degrees 2-theta and a PXRD pattern as depicted in FIG. 6 or FIG. 6A.

Crystalline form V of tafamidis may be an anhydrous form or a solvated form. In specific embodiments, crystalline form V may be an anhydrous form or a methanol solvate.

Crystalline form V of tafamidis may alternatively be characterized by a PXRD pattern having peaks at 6.0, 17.8, 19.9, 20.6, 23.9, 25.8, 27.3, 29.2 and 31.1 degrees 2-theta±0.2 degrees 2-theta.

In any embodiment of the invention, crystalline form V may be an anhydrous form or a methanol solvate.

In any embodiment of the present invention anhydrous Form V of tafamidis may alternatively or additionally be characterized by a solid state $^{13}$C NMR spectrum having peaks at 171.5, 161.0, 149.1, 144.7, 131.0±0.2 ppm. Anhydrous Form V of tafamidis may alternatively or additionally be characterized by a solid state $^{13}$C NMR spectrum having the following chemical shift absolute differences from a reference peak at 109.5 ppm±0.2 ppm of 62.1, 51.6, 39.6, 35.2, 21.5±0.1 ppm. In any embodiment of the present invention, anhydrous Form V of tafamidis may alternatively or additionally be characterized by a solid state $^{13}$C NMR spectrum substantially as depicted in FIG. 8.

The present disclosure also provides the use of the solid state forms of tafamidis and tafamidis salts for preparing other solid state forms of tafamidis, tafamidis salts and solid state forms thereof.

The present disclosure further encompasses processes for preparing other solid state forms of tafamidis, or solid state forms thereof, as well as other tafamidis salts or solid state forms thereof. The process includes preparing the solid state form of the present disclosure, and converting it to other solid state forms of tafamidis. Alternatively, the process includes preparing the solid state form of the present disclosure, and converting it to tafamidis salt. The conversion can be done, for example, by a process including reacting the obtained tafamidis with an appropriate base such as meglumine, alkali/alkaline earth metal bases such as potassium, sodium, calcium, magnesium, ammonia or alkyl amines (in embodiments $C_{1-6}$ mono-, di- or trialkylamines). In embodiments, the alkali/alkaline earth metal bases are selected from the group consisting of potassium hydroxide, potassium carbonate, potassium hydrogen carbonate, sodium hydroxide, sodium carbonate, sodium hydrogen carbonate, calcium hydroxide or magnesium hydroxide.

In another embodiment the present disclosure encompasses the above described solid state forms of tafamidis and salts thereof, for use in the preparation of pharmaceutical compositions and/or formulations, in embodiments for the treatment of transthyretin-mediated amyloidosis. In embodiments the present disclosure encompasses the use of the above described solid state forms of tafamidis and salts thereof for the preparation of a pharmaceutical composition comprising tafamidis or salt thereof.

In another embodiment the present disclosure encompasses the use of the above described solid state forms of tafamidis and salts thereof, or combinations thereof, for the preparation of pharmaceutical compositions and/or formulations, in embodiments oral formulations, e.g., tablets or capsules. In embodiments the present disclosure encompasses the above described solid state forms of tafamidis and/or salts thereof, for the preparation of a pharmaceutical composition or formulation, in embodiments an oral formulation in the form of a dispersion including tafamidis or salt thereof.

The present disclosure further provides pharmaceutical compositions including the solid state forms of tafamidis and salts thereof, or combinations thereof, according to the present disclosure.

In yet another embodiment, the present disclosure encompasses pharmaceutical formulations including at least one of the above described solid state forms of tafamidis and/or salts thereof, and at least one pharmaceutically acceptable excipient.

Pharmaceutical formulations of the present disclosure contain any one or a combination of the solid state forms of tafamidis of the present disclosure. In addition to the active ingredient, the pharmaceutical formulations of the present disclosure can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g.

Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present disclosure include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present disclosure, the active ingredient and any other solid excipients are dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present disclosure include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present disclosure can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiments the route of administration is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, in embodiments a powdered or granulated solid composition of the disclosure, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, in embodiments water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present disclosure can include any of the aforementioned blends and granulates that were described with reference to tableting, but they are not subjected to a final tableting step.

A pharmaceutical formulation of tafamidis may be formulated for administration to a mammal, in embodiments a human. Tafamidis can be formulated, for example, as a viscous liquid solution or suspension, in embodiments a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others, including those disclosed in Ansel et al., Pharmaceutical Dosage Forms and Drug Delivery Systems, 7th ed. The present disclosure encompasses a process to prepare said formulations of tafamidis by combining at least one of the above solid state forms and at least one pharmaceutically acceptable excipient.

The solid state forms as defined herein, as well as the pharmaceutical compositions or formulations of tafamidis can be used as medicaments, in embodiments for the treatment of transthyretin-mediated amyloidosis.

The present disclosure also provides a method of treating transthyretin-mediated amyloidosis, by administering a therapeutically effective amount of the solid state form of tafamidis of the present disclosure, or at least one of the above pharmaceutical compositions or formulations, to a subject suffering from transthyretin-mediated amyloidosis, in embodiments cardiomyopathy of wild type or hereditary transthyretin-mediated amyloidosis, or transthyretin amyloidosis in adult patients with stage 1 symptomatic polyneuropathy, to delay peripheral neurologic impairment or otherwise in need of the treatment.

The present disclosure also provides the use of the solid state forms of tafamidis of the present disclosure, or at least one of the above pharmaceutical compositions or formulations for the manufacture of a medicament for treating transthyretin-mediated amyloidosis, in embodiments cardiomyopathy of wild type or hereditary transthyretin-mediated amyloidosis, or transthyretin amyloidosis in adult patients with stage 1 symptomatic polyneuropathy, to delay peripheral neurologic impairment.

Having described the invention with reference to certain preferred embodiments, other embodiments will become apparent to one skilled in the art from consideration of the specification. The invention is further illustrated by reference to the following examples describing in detail the preparation of the composition and methods of use of the composition. It will be apparent to those skilled in the art that many modifications, both to materials and methods, may be practiced without departing from the scope of the disclosure.

Analytical Methods

Powder X-Ray Diffraction Pattern ("PXRD") Method:

Sample after being powdered in a mortar and pestle is applied directly on a silicon plate holder. The X-ray powder diffraction pattern was measured with Philips X'Pert PRO X-ray powder diffractometer, equipped with Cu irradiation source=1.54184 Å(Ångström), X'Celerator (2.022° 2θ) detector. Scanning parameters: angle range: 3-40 deg., step size 0.0167, time per step 37 s, continuous scan.

$^{13}$C Solid State Nuclear Magnetic Resonance ("Ss-NMR" or $^{13}$C Solid State NMR) Method Solid state NMR spectra was measured at 11.7 T using a Bruker Avance III HD 500 US/WB NMR spectrometer (Karlsruhe, Germany, 2013). The $^{13}$C CP/MAS NMR spectra employing cross-polarization were acquired using the standard pulse scheme at spinning frequency of 11 kHz. The recycle delay was 8 s and the cross-polarization contact time was 2 ms. The strength of spin-locking fields $B_1$ ($^{13}$C) expressed in frequency units $\omega 1/2\pi=\gamma B1$ was 64 kHz.

The $^{13}$C NMR scale was referenced to α-glycine (176.03 ppm). Frictional heating of the spinning samples was offset by active cooling, and the temperature calibration was performed with $Pb(NO_3)_2$. The NMR spectrometer was completely calibrated and all experimental parameters were carefully optimized prior the investigation. Magic angle was set using KBr during standard optimization procedure and homogeneity of magnetic field was optimized using adamantane sample (resulting line-width at half-height Δv1/2 was less than 3.5 Hz at 250 ms of acquisition time).

EXAMPLES

Tafamidis can be prepared according to the procedure described in U.S. Pat. No. 7,214,695.

Example 1: Preparation of Amorphous Tafamidis

Tafamidis (2.730 grams) was subjected to milling in ball mill (agate jar, 3 agate balls φ=7 mm, frequency: 25 Hz, time: 6 h). Obtained solid was analyzed. Amorphous form of Tafamidis was confirmed by PXRD.

Example 2: Preparation of Tafamidis Form I

Tafamidis amorphous form obtained according to Example 1 (100 mg) was exposed to water/acetone solvent mixture (volume ratio water/acetone=97/3) vapour for 33 days at 25° C. Obtained solid was analyzed. Tafamidis Form I was confirmed by PXRD.

Example 3: Preparation of Tafamidis Form I

Tafamidis amorphous form obtained according to Example 1 (100 mg) was exposed to water/methanol solvent mixture (volume ratio water/methanol=99/1) vapour for 33 days at 25° C. Obtained solid was analyzed. Tafamidis Form I was confirmed by PXRD.

Example 4: Preparation of Tafamidis Form I

Tafamidis amorphous form obtained according to Example 1 (100 mg) was exposed to water vapour for 33 days at 25° C. Obtained solid was analyzed. Tafamidis Form I was confirmed by PXRD.

Example 5: Preparation of Tafamidis Form I

Tafamidis amorphous form obtained according to Example 1 (100 mg) was exposed to 100% of relative humidity at 25° C., for 30 days. Obtained solid was analyzed. Tafamidis Form I was confirmed by PXRD.

Example 6: Preparation of Tafamidis Form I

Tafamidis (1000 mg) was dissolved in 50 ml of tetrahydrofuran (THF) at room temperature. Obtained solution was added dropwise to 200 ml of water cooled to temperature of 10° C. The crystallization was obtained momentarily and suspension was mixed additionally for one hour. Obtained solid was isolated by vacuum filtration (973 mg), and analyzed by PXRD. Tafamidis Form I was obtained.

Example 7: Preparation of Tafamidis Form II

Tafamidis (122 mg) was dissolved in 7 mL of 2-methyl tetrahydrofuran at 61° C. Obtained solution was crash cooled in cold bath, and at 7° C. the crystallization was obtained. Obtained solid was isolated by vacuum filtration (33 mg), and analyzed by PXRD. Tafamidis Form II was obtained.

Example 8: Preparation of Tafamidis Form II

Tafamidis (20 mg) was dissolved in 4 mL of 2-methyl tetrahydrofuran at 25° C. Obtained solution was left to slowly evaporate at room temperature by loosely attaching the lid for 7 days. Obtained solid was analyzed by PXRD. Tafamidis Form II was obtained.

Example 9: Preparation of Tafamidis Form III

Tafamidis (20 mg) was dissolved in acetic acid (6 ml) at reflux temperature (118° C.). Obtained solution was left to slowly evaporate. After 24 hours crystallization was obtained. Obtained solid was isolated by vacuum filtration and analyzed by PXRD. Tafamidis Form III was obtained.

Example 10: Preparation of Tafamidis Form III

Tafamidis (100 mg) was subjected to milling in ball mill (agate jar, 5 agate balls φ=7 mm, frequency: 25 Hz, time: 30 minutes). Acetic acid was added dropwise (three drops) in ball mill. Obtained solid was analyzed by PXRD. Tafamidis Form III was obtained.

Example 11: Preparation of Tafamidis Form III

Tafamidis (113 mg) was dissolved in 20.5 mL of acetic acid at 92° C. Obtained solution was crash cooled in cold bath, and at 65° C. the crystallization was obtained. Obtained solid was isolated by vacuum filtration (75 mg), and analyzed by PXRD. Tafamidis Form III was obtained.

Example 12: Preparation of Tafamidis Form III

Tafamidis (100 mg) was stirred in 1 mL of acetic acid at room temperature (25° C.). Obtained solid was analyzed by PXRD after 4 hours Tafamidis Form III was obtained.

Example 13: Preparation of Tafamidis Form III

Tafamidis (100 mg) was stirred in 1 mL of acetic acid at 50° C. Obtained solid was analyzed by PXRD after 2 hours. Tafamidis Form III was obtained.

Example 14: Preparation of Tafamidis Form IV

Tafamidis (511 mg,) was dissolved in acetic acid (35 ml) at a temperature of 105° C. Obtained solution was slow (spontaneously) cooled. Crystallization was obtained at 89° C. Suspension was stirred for one hour and then isolated by vacuum filtration (495 mg). Obtained solid was analyzed by PXRD. Tafamidis Form IV (acetic acid solvate) was obtained.

Example 15: Preparation of Tafamidis Form V

Tafamidis (172 mg) was dissolved in THF (12 ml) at room temperature. Antisolvent (Methanol) was cooled to 0° C. (ice bath) and added dropwise into solution (48 ml). Crystallization was momentary. Suspension was stirred for one hour and then isolated by vacuum filtration (108 mg). Obtained solid was washed with solvent mixture THF: Methanol (1:4). Obtained solid was analyzed by PXRD. Tafamidis Form V was obtained.

Example 16: Preparation of Tafamidis Form 4

Form II (2-Methyl THF solvate) obtained from crash cooling crystallization (Example 7) was dried in vacuum dryer at 150° C. for 20 minutes. Obtained solid was analyzed by PXRD. Pure Form 4 was obtained (HPLC purity: 99.99%).

Example 17: Preparation of Tafamidis Form 4

Form III (Acetic acid solvate) obtained from crash cooling crystallization (Example 11) was dried in vacuum dryer at 100° C. for 1 hour. Obtained solid was analyzed by PXRD. Pure Form 4 was obtained.

Example 18: Preparation of Tafamidis Form 4

Form IV (Acetic acid solvate) was dried in a vacuum dryer at 80° C. After 5 hours Form IV started to convert to mixture of Form IV and Form 4. The sample was left to dry for 22 hours. Obtained solid was analyzed by PXRD. The result was pure Form 4.

Example 19: Preparation of Tafamidis Form 4

Form I (hydrate form), obtained from solvent antisolvent reverse crystallization (Example 6), was dried in vacuum dryer at 150° C. for 20 minutes. Obtained solid was analyzed by PXRD. Pure Form 4 was obtained.

Example 20: Preparation of Tafamidis Form 4

Form V obtained from solvent antisolvent crystallization (Example 15), was heated in DSC up to 160° C., for 10 minutes. Obtained solid was analyzed by PXRD. Pure Form 4 was obtained.

Example 21: Preparation of Tafamidis Form V

Tafamidis (1.0 gram, 3.25 mmol, Form 1) was dissolved in mixture of solvents toluene/NMP (15 V; 15% NMP) by heating up to 70-75° C. The solution was spontaneously cooled down to 30° C. and slowly added to cold methanol (30 V) at 0-5° C. Crystallization was momentary. The obtained suspension was stirred at 0-5° C. for 2 hours. The obtained crystals were isolated by vacuum filtration. Obtained solid was washed with methanol (10 V) and dried in vacuum dryer at 80° C., 20 mbar for 6 hours (0.9 grams of crystals was obtained, chrom. purity 99%). Obtained solid was analyzed by PXRD. Tafamidis form V was obtained.

Example 22: Preparation of Tafamidis Form V

Tafamidis (498 mg, Form 1) was dissolved in THF (28 ml) at room temperature. Antisolvent (Methanol) was cooled to 0° C. (ice bath) and added dropwise into solution (92 ml). Crystallization was momentary. Suspension was stirred for one hour and then isolated by vacuum filtration (427 mg). Obtained solid was washed with solvent mixture THF: Methanol (1:4). Obtained solid was analyzed by XRD. Tafamidis form V (Methanol solvate) was obtained. Obtained solid was subjected to heating in vacuum dryer at 80° C. for 2 hours. Obtained solid was analyzed by PXRD. Tafamidis Form V (anhydrous) was obtained.

Example 23: Preparation of Tafamidis Anhydrous Form V 4-(3,5-dichlorobenzamido)-3-hydroxybenzoic acid (25.00 grams; 76.7 mmol), toluene (281.3 ml), N-methylpyrrolidone (93.8 ml) and methanesulfonic acid (14.9 ml; 230.0 mmol: 3.0 eq) were charged into reactor at 20-25° C. The reaction mixture was heated to reflux temperature (117-119° C.) and stirred until the reaction was completed (about 15 hours). The reaction mixture was then cooled down to 100-110° C. and pH was adjusted to 1.4-1.8 with triethylamine addition (32 ml; 230.0 mmol; 3.0 eq.). The reaction mixture was added dropwise to cold methanol (750 ml; previously cooled down to 0-5° C.) during 1 hour. Crystallization occurred. The suspension was stirred at 0-5° C. for additional 3 hours. Crystals of Tafamidis methanol solvate were filtered off over Buchner funnel and washed with methanol (2×100 ml). Wet crystals were suspended in fresh methanol (375 ml) at 20-25° C. for 3-6 h. Crystals of Tafamidis methanol solvate were filtered off over Buchner funnel, washed with methanol (2×50 ml) and dried at 80° C., 20 mbar, 10 hours. White crystals of Tafamidis anhydrous form V were obtained.

Example 24: Preparation of Tafamidis Form III

Tafamidis (100 mg) was stirred in 1 mL of acetic acid at room temperature (25° C.) for 4 hours. The mixture was filtered and the obtained solid was analyzed by PXRD. Tafamidis Form III was obtained.

Example 25: Preparation of Tafamidis Form III

Tafamidis (100 mg) was stirred in 1 mL of acetic acid at 50° C. for 2 hours. The mixture was filtered and the obtained solid was analyzed by PXRD. Tafamidis Form III was obtained.

The invention claimed is:

1. A crystalline form of tafamidis designated as form V, which is characterized by
   a PXRD pattern having peaks at 6.0, 19.9, 20.6, 23.9 and 29.2 degrees 2-theta±0.2 degrees 2-theta.

2. The crystalline form of tafamidis according to claim 1, which is characterized by at least one of:
   a PXRD pattern substantially as depicted in FIG. 6; or
   a PXRD pattern substantially as depicted in FIG. 6A.

3. The crystalline form of tafamidis according to claim 1, which is characterized by a PXRD pattern having peaks at 6.0, 19.9, 20.6, 23.9 and 29.2 degrees 2-theta±0.2 degrees 2-theta, and also having one, two, three or four additional peaks at 17.8, 25.8, 27.3 and 31.1 degrees 2-theta±0.2 degrees 2-theta.

4. The crystalline form of tafamidis according to claim 1, characterized by a PXRD pattern having peaks at 6.0, 17.8, 19.9, 20.6, 23.9, 25.8, 27.3, 29.2 and 31.1 degrees 2-theta±0.2 degrees 2-theta.

5. The crystalline form of tafamidis according to claim 1, which is a methanol solvate.

6. The crystalline form of tafamidis according to claim 1, which is an anhydrous form or a solvated form.

7. The crystalline form of tafamidis according to claim 1, which is an anhydrous form.

8. A pharmaceutical composition comprising the crystalline form of tafamidis according to claim 1.

9. The pharmaceutical composition according to claim 8, which is in the form of a dispersion.

10. A pharmaceutical formulation comprising the crystalline form of tafamidis according to claim 1, and at least one pharmaceutically acceptable excipient.

11. The pharmaceutical formulation according to claim 10, which is an oral formulation.

12. A process for preparing a pharmaceutical formulation comprising combining the crystalline form of tafamidis according to claim 1 with at least one pharmaceutically acceptable excipient.

13. A medicament comprising the crystalline form of tafamidis according to claim 1.

14. A method of treating transthyretin-mediated amyloidosis in a subject in need thereof, comprising administering a therapeutically effective amount of the crystalline form of tafamidis of claim 1 to the subject, wherein the subject is suffering from familial amyloid polyneuropathy, cardiomyopathy of wild type or hereditary transthyretin-mediated amyloidosis, or transthyretin amyloidosis in adult patients with stage 1 symptomatic polyneuropathy.

15. The crystalline form of tafamidis according to claim 1, which is further characterized by at least one of:
   (a) a solid state $^{13}$C NMR spectrum having peaks at 171.5, 161.0, 149.1, 144.7, 131.0±0.2 ppm;
   (b) a solid state $^{13}$C NMR spectrum having the following chemical shift absolute differences from a reference peak at 109.5 ppm±0.2 ppm of 62.1, 51.6, 39.6, 35.2, 21.5±0.1 ppm; or
   (c) a solid state $^{13}$C NMR spectrum substantially as depicted in FIG. 8.

* * * * *